(12) United States Patent  
Decuzzi et al.

(10) Patent No.: US 8,361,508 B2  
(45) Date of Patent: Jan. 29, 2013

(54) ENDOCYTOTIC PARTICLES

(75) Inventors: Paolo Decuzzi, Bari (IT); Mauro Ferrari, Houston, TX (US)

(73) Assignees: Board of Regents of the University of Texas System, Austin, TX (US); The Ohio State University Research Foundation, Columbus, OH (US)

( * ) Notice: Subject to any disclaimer, the term of this patent is extended or adjusted under 35 U.S.C. 154(b) by 908 days.

(21) Appl. No.: 12/034,259

(22) Filed: Feb. 20, 2008

(65) Prior Publication Data

US 2008/0206344 A1    Aug. 28, 2008

Related U.S. Application Data

(60) Provisional application No. 60/891,584, filed on Feb. 26, 2007.

(51) Int. Cl.
*A61K 9/14* (2006.01)
*A61K 33/00* (2006.01)
*C12Q 1/02* (2006.01)

(52) U.S. Cl. ........... 424/489; 424/600; 435/29; 435/375

(58) Field of Classification Search ........................ None
See application file for complete search history.

(56) References Cited

U.S. PATENT DOCUMENTS

| | | | |
|---|---|---|---|
| 4,520,110 | A | 5/1985 | Stryer et al. |
| 4,888,176 | A | 12/1989 | Langer et al. |
| 4,933,185 | A | 6/1990 | Wheatley et al. |
| 5,010,167 | A | 4/1991 | Ron et al. |
| 6,107,102 | A | 8/2000 | Ferrari |
| 6,355,270 | B1 | 3/2002 | Ferrari et al. |
| 7,091,041 | B2 | 8/2006 | Monahan et al. |
| 2003/0114366 | A1* | 6/2003 | Martin et al. .................... 514/12 |
| 2008/0102030 | A1 | 5/2008 | Decuzzi et al. |
| 2008/0311182 | A1 | 12/2008 | Ferrari et al. |

FOREIGN PATENT DOCUMENTS

| | | | |
|---|---|---|---|
| WO | 03029403 | A2 | 4/2003 |
| WO | WO 2006/086257 | A2 | 8/2006 |
| WO | WO 2007/120248 | A2 | 10/2007 |

OTHER PUBLICATIONS

Decuzzi et al., The role of specific and non-specific interactions in receptor-mediated endocytosis of nanoparticles, Biomaterials 28 (2007) 2915-2922.*

Decuzzi et al "Adhesion of Microfabricated Particles on Vascular Endothelium: A Parametric Analysis," Annals of Biomedical Engineering, vol. 32, No. 6, Jun. 2004, pp. 793-802.*

Gao et al "Mechanics of receptor-mediated endocytosis," PNAS 102(27): 9469-9474 (2005).*

Cohen et al., "Microfabrication of Silicon-Based Nanoporous Particulates for Medical Applications," Biomedical Microdevices, 2003, 5(3):253-259.

Decuzzi et al., "The adhesive strength of non-spherical particles mediated by specific interactions," Biomaterials, 2006, 27:5307-5314.

Decuzzi et al., "Adhesion of Microfabricated Particles on Vascular Endothelium: A Parametric Analysis,"Annals of Biomedical Engineering, Jun. 2004, 32(6):793-802.

Decuzzi et al., "A Theoretical Model for the Margination of Particles within Blood Vessels," Annals of Biomedical Engineering, Feb. 2005, 33(2):179-190.

Decuzzi et al., "The Effective Dispersion of Nanovectors Within the Tumor Microvasculature," Annals of Biomedical Engineering, Apr. 2006, 34(4):633-641.

Decuzzi et al., "The role of specific and non-specific interactions in receptor-mediated endoxytosis of nanoparticles," Biomaterials, 2007, 28:2915-2922.

Gao et al., "Mechanics of receptor-mediated endocytosis," Proc. Natl. Acad. Sci. USA, Jul. 5, 2005, 102(27):9469-9474.

Hochmuth, R.M., "Micropipette aspiration of living cells," J. Biomech., 2000, 33:15-22.

Mukherjee et al., "Endocytosis," Physiol. Rev., Jul. 1997, 77(3):759-803.

Oberdorster et al., "Nanotoxicology: An Emerging Discipline Evolving from Studies of Ultrafine Particles," Environ. Health Perspect., Jul. 2005, 113(7):823-839.

Paik et al., "Micromachining of mesoporous oxide films for microelectromechanical system structures," J. Mater. Res., Aug. 2002, 17(8):2121-2129.

Panes et al., "Regional differences in constitutive and induced ICAM-1 expression in vivo," Am. J. Physiol., 1995; 269(6Pt2):H1955-1964.

Prodan et al., "Low-frequency, low-field dielectric spectroscopy of living cell suspensions," Journal of Applied Physics, Apr. 1, 2004, 95(7):3754-3756.

Taylor, R., Ed., Protein Immobilization Fundamentals and Applications, 1991, 109-110.

Vasir et al., "Polymeric nanoparticles for gene delivery," Expert Opin. Drug Deliv., 2006, 3(3):325-344.

PCT Search Report for International Application No. PCT/US2008/054413, dated Jul. 4, 2008.

* cited by examiner

*Primary Examiner* — Suzanne Ziska
(74) *Attorney, Agent, or Firm* — Winstead PC (57) ABSTRACT

Endocytosis of an active agent into a cell having surface receptors can be enhanced by using particles that have a radius no less than an endocytotic threshold determined based on a surface density of the receptors, a surface density of the moieties and interaction parameters that include at least one of a receptor-moiety spring constant and a non-specific interaction strength.

32 Claims, 3 Drawing Sheets

ENDOCYTOTIC PARTICLES

CROSS REFERENCE TO RELATED APPLICATIONS

The present application claims the benefit under 35 U.S.C. §119(e) of U.S. Provisional Patent Application No. 60/891,584 filed Feb. 26, 2007, which is incorporated herein by reference in its entirety.

FIELD

The invention relates generally to compositions and methods utilizing micro or nanoparticles for delivery of active agents, such as therapeutic or imaging agents, and more particularly to compositions and methods utilizing micro or nanoparticles for delivery of active agents inside cells.

BACKGROUND

Endocytosis is a general term defining processes, by which a cell imports selected extracellular species, such as molecules, viruses, particles and microorganisms and target them to specific organelles within a cytoplasm. Particle endocytosis can be of fundamental importance in several applications including drug and gene delivery and nanotoxicology, see e.g. Vasir J. K., Labhasetwar V., Expert Opin. Drug Deliv. 2006; 3(3):325-44, and Oberdorster G., et al., Environ. Health Perspect. 2005; 113(7):823-39. Endocytosis can occur through a variety of pathways including clathrin-dependent and independent receptor-mediated endocytosis, pinocytosis and phagocytosis.

A receptor-mediated endocytosis (RME) is an effective mechanism for cellular uptake of micrometric and sub-micrometric particles that have grafted or non-specifically adsorbed on their surfaces molecules, such as ligands, that are capable of binding specifically to countermolecules, such as receptors, expressed on the cell's membrane. The receptors can enter the cell by membrane invagination together with the particles. During the RME, the receptors expressed over the cell membrane can be collected at the site of invagination by surface diffusion, a process without which endocytosis would not occur or would have occurred over a much longer time scale. A detailed review of different endocytotic mechanisms and features can be found, for example, in Mukherjee S., et al. Physiol. Rev. July 1997; 77(3):759-803.

Gao, Shi and Freund proposed a mathematical model for the receptor-mediated endocytosis of particles, see Gao H., Shi W., Freund L. B., Proc. Natl. Acad. Sci. USA, 2005 5; 102(27):9469-74, 2005, which showed that a threshold particle radius may exist, below which endocytosis is not energetically favorable; and an optimal particle radius may exist, slightly larger than the threshold radius, for which a characteristic time for particle wrapping is minimized. Consequently, it was speculated that particles with a size smaller than the threshold radius can never be internalized by receptor mediated endocytosis, whereas particles with a size equal to the optimal particle radius are the fastest to be internalized. The work of Gao and colleagues, however, suffers from at least one drawback: it does not take into account non-specific interactions that arise on the cell-particle interface. There is continuing interest in the development of ways to enhance endocytosis of specified particles into cells.

SUMMARY

According to one embodiment, a method of enhancing an endocytosis of an active agent into a cell having surface receptors, comprises obtaining particles comprising the active agent and surface moieties with affinity for the receptors, wherein the particles have a radius no less than an endocytotic threshold radius determined based on (a) a surface density of the receptors, (b) a surface density of the moieties and (c) interaction parameters including at least one of a receptor-moiety spring constant between said receptors and said moieties and a non-specific interaction strength between said cell and one of the particles.

According to another embodiment, a method of treating or monitoring a physiological condition comprises selecting a target site affected by the condition in a body of a subject in need thereof such that the target site has surface receptors; and administering to the subject an effective amount of a composition comprising particles that comprise at least one active agent and that have a surface with moieties having affinity for the receptors, wherein at least 10% of the particles have a radius substantially equal to an endocytosis maximizing radius determined based on a surface density of the receptors, a surface density of the moieties and interaction parameters including at least one of a receptor-moiety spring constant between said receptors and said moieties and a non-specific interaction strength between a cell of the target site and one of said particles. Thus, embodiments described herein comprise a combination of features and advantages intended to address various shortcomings of the prior art. The various characteristics described above, as well as other features, will be readily apparent to those skilled in the art upon reading the following detailed description of the preferred embodiments, and by referring to the accompanying drawings.

DETAILED DESCRIPTION

The following research articles and patent documents, which are all incorporated herein in their entirety, may be useful for understanding the invention: (1) P. Decuzzi and M. Ferrari, Biomaterials 28 (2007) 2915-2922; (2) P. Decuzzi and M. Ferrari, Biomaterials 27 (2006) 5307-5314; (3) P. Decuzzi et al. Annals of Biomedical Engineering 33 (2005) 179-190; (4) P. Decuzzi et al. Annals of Biomedical Engineering 34 (2006) 633-641; (5) P. Decuzzi et al., Annals of Biomedical Engineering 32 (2004) 793-802; (6) U.S. patent application Ser. No. 11/836,004 filed Aug. 8, 2007 to Ferrari; (7) PCT application no. PCT/US2006/03986 filed Sep. 27, 2006 to Decuzzi and Ferrari; and (8) U.S. patent application Ser. No. 11/870,077 filed to Decuzzi and Ferrari on Oct. 10, 2007.

DEFINITIONS

Unless otherwise specified "a" or "an" means one or more.
Unless otherwise specified the terms "endocytosis" and "endocytotic" mean receptor mediated endocytosis and receptor mediated endocytotic respectively.

Endocytotic threshold size or radius means that a particle having a size or radius less than the endocytotic threshold size will not be able to enter a cell via a receptor mediated endocytosis.

Endocytosis maximizing size or radius means that a particle having such a size or radius that can minimize the particle's wrapping time into a cell during a receptor mediated endocytosis.

"Microparticle" refers to a particle having a maximum dimension from 1 micrometer to 1000 micrometers, or, in some embodiments from 1 micron to 100 microns as specified.

"Nanoparticle" refers to a particle having a maximum dimension of less than 1 micron.

DISCLOSURE

The inventors have recognized the importance of non-specific interactions at a cell-particle interface for receptor mediated endocytosis. Accordingly, an endocytotic threshold radius or an endocytotic maximizing radius can depend on at least one of a spring constant between receptors on the cell's surface and moieties on the particle's surface and a non-specific interaction strength between the cell and the particle.

Thus, in one embodiment, the invention provides a method of enhancing an endocytosis of an active agent into a cell having surface receptors on its membrane. The method involves obtaining endocytotic particles that comprise the active agent and have on their surfaces surface moieties with affinity for or which are capable of binding to the receptors.

In another embodiment, the invention provides a method of treating or monitoring a physiological condition. The method involves selecting in a body of a subject, such as a mammal, preferably a human, a target site, that is affected by the physiological condition and has surface receptors on its surface, and administering to the subject an effective amount of a composition that comprises endocytotic particles that comprise the active agent and have on their surfaces surface moieties with affinity for or capable of binding to the receptors.

The endocytotic particles have a size or radius greater than an endocytosis threshold size or radius that is determined based on a surface density of the receptors on the cell or the target cite, a surface density of the moieties on the particle and interaction parameters between the cell and the particle provided that such interaction parameters include at least one of a spring constant between the receptor and the moiety or a non-specific interaction strength between the cell and the particle. Preferably, the endocytotic particles have a size or radius substantially equal to an endocytosis maximizing radius that is determined based on the surface density of the receptors on the cell or the target cite, the surface density of the moieties on the particle and interaction parameters between the cell and the particle, provided that such interaction parameters include at least one of a spring constant between the receptor and the moiety or a non-specific interaction strength between the cell and the particle.

The physiological condition that can be monitored or treated by the endocytotic particles can be any condition that requires delivery of the active agent inside the cell. For example, the physiological condition can be a disease, such as cancer or an inflammation.

The selected target site can be a vasculature site, such as a coopted vasculature; an angiogenic vasculature or a renormalized vasculature, which has molecular receptors on its surface. For a coopted vasculature, the receptors can be angiopoietin 2 receptors; for an angiogenic vasculature, the receptors can be vascular endothelial growth factors (VEGF), basic fibroblast growth factors or endothelial markers such as $\alpha_v\beta_3$ integrins; for renormalized vasculature, the receptors can be carcinoembrionic-related cell adhesion molecules 1 (CEACAM1), endothelin-B receptor (ET-B), vascular endothelial growth factor inhibitors gravin/AKAP12, scaffolding proteins for protein kinase A and protein kinase C.

Surface moieties on the particle can be selected to be complimentary to the receptors. Such surface moieties can be, for example, antibodies, aptamers or ligands with affinity for or capable of binding to the receptors.

The composition administered to the subject can further comprise non-endocytotic particles. Preferably, the endocytotic particles constitute at least 10%, or at least 25% or at least 75% or at least 90% by number of the total number of particles in the composition.

The following disclosure illustrates determining an endocytotic threshold radius and an endocytotic maximizing radius for a cylindrical particle, however, it should be understood that similar methods can be applied for particles of other shapes as well.

Cylindrical Particle

Figure 1:
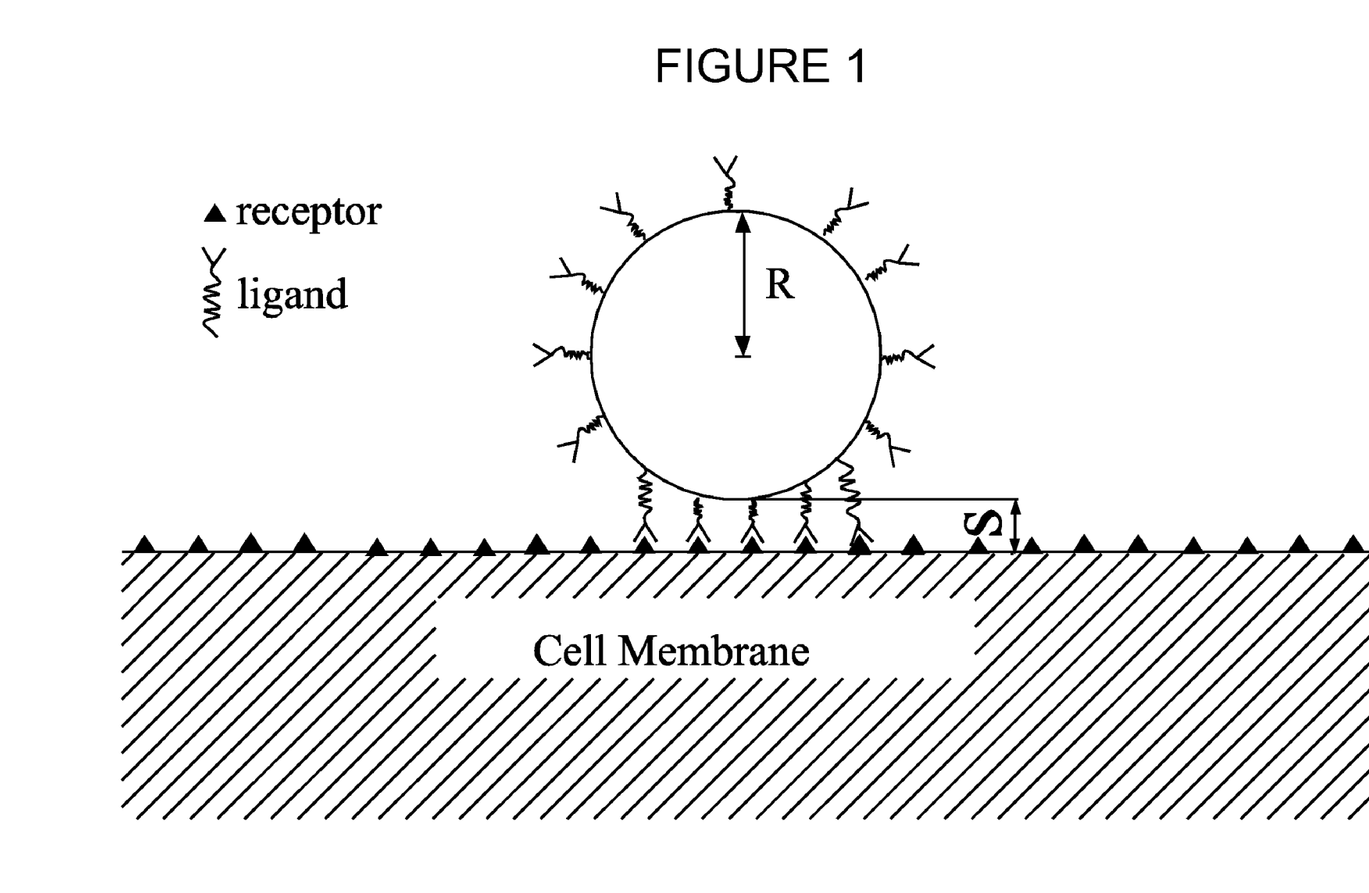
FIG. 1 schematically depicts a cylindrical particle decorated with ligand molecules interacting specifically with receptor molecules expressed on a cell membrane.

FIG. 1 illustrates a cylindrical particle having on its surface ligands that interact with countermolecules (receptors) on a cell membrane. A surface density of the ligands is $m_l$, while the surface density of the receptors is $m_r$.

An endocytotic threshold radius for the cylindrical particle can be determined by solving equation (1) by imposing $\alpha=0$ $$\left[\left(C - \frac{1}{2}G(\tilde{s}_{eq} - \tilde{\xi})^2\right) - \frac{F}{\tilde{s}_{eq}}\exp[-\tilde{s}_{eq}] - \frac{L}{\tilde{s}_{eq}^2} - H^2 + \ln\frac{\tilde{m} - g(\alpha)}{1 - g(\alpha)}\right] \quad (1)$$
$$[1 - g(\alpha)] + 1 - \tilde{m} = 0$$

where $g(\alpha)=\sqrt{\pi}\alpha e^{\alpha^2}\text{erfc}[\alpha]$ and $\tilde{s}_{eq}$ is a solution of equation (2)

$$G(\tilde{s}_{eq} - \tilde{\xi}) - F\left(\frac{\tilde{s}_{eq} + 1}{\tilde{s}_{eq}^2}\right)\exp[-\tilde{s}_{eq}] - \frac{2L}{\tilde{s}_{eq}^3} = 0 \quad (2)$$

In the equations (1) and (2), $$\tilde{\xi} = \xi/\delta; \ \tilde{m}_r/m_l; \ G = \frac{k\delta^2}{k_BT}; \ F = \frac{1}{k_BT}\frac{\sigma}{\delta m_l};$$
$$H = \frac{1}{R}\sqrt{\frac{B}{2m_l}}; \text{ and } L = \frac{c_{fl}}{m_l B\delta^2},$$

where $k_B$ is the Bolzmann's constant and T is the absolute temperature of the cell or of the target site.

Parameters $\delta$, $\xi$, k, $m_r$, $m_l$, $\sigma$, B and C can be determined prior to obtaining the particles based on the nature of the receptors and the ligands.

C is the ligand-receptor binding energy relative to $k_BT$. C depends on a particular ligand-receptor pair. In particular, $C=\log [K_d^{2D}]$, $K_d^{2D}$ is an equilibrium dissociation constant for the ligand-receptor interacting at the cell/particle interface. $K_d^{2D}$ can be estimated from the following relation $K_d^{2D}=K_d/h$, where $K_d$ is an equilibrium dissociation constant for the same ligand-receptor pair determined, for example, experimentally in solution and h is a thickness of a confinement region, to which the ligand-receptor sites are restricted. In many cases, h can be equal approximately to 10 nm.

B is a bending energy factor of the cell's membrane, which can be determined as detailed in Hochmuth, R. M., J. Biomech., 33:15-22, 2000.

$m_r$, the surface density on the receptors, can be determined using methods known to those of ordinary skill in the art. For example, one can determine $m_r$ in vivo by using radiolabeled monoclonal antibodies complimentary to the receptors as detailed for intercellular adhesion molecule 1 receptors in Panes J., et al. Am. J. Physiol. 1995; 269(6Pt2):H1955-64. Alternatively, $m_r$ can be determined using fluorescently labeled monoclonal antibodies complementary to the receptors. Such fluorescently labeled monoclonal antibodies can be antibodies labeled with phycoerythrin, as disclosed in U.S. Pat. No. 4,520,110.

$m_l$, the surface density of ligands, can be varied by controlling surface functionalization conditions for the particle and/or by varying a size of the ligand molecule. The actual surface density of ligands on the particle can be verified experimentally using citofluometry or radiolabeled countermolecules in radioassays.

Parameters $\xi$ (a ligand-receptor natural length) and k (a ligand receptor spring constant) can be determined for a particular ligand-receptor pair using atomic force microscopy.

$\delta$, a characteristic decay length of non-specific interactions, and $\sigma$, a stiffness parameter of non-specific interactions, appearing in a compact expression for the non-specific interaction force $F_{NS}$ $$F_{NS} = \sigma \frac{s+\delta}{s^2\delta} \exp\left[-\frac{s}{\delta}\right] \quad (3)$$

can be determined by fitting the above relation (3) with the following explicit relation (4) for the non-specific interaction force $F_{NS}$ $$F_{NS} = 2\pi\left(\frac{3}{4\pi}\right)^{1/3}\left[\frac{A}{12\pi s^2} + \frac{64}{\kappa}k_B T\rho_\infty \varepsilon_v \varepsilon_c e^{-\kappa s} - 36\Gamma k_B T e^{-s/R_g}\right]V^{1/3} \quad (4)$$

where V is the volume of the particle.

A is a Hamacker constant, which can be estimated as using the following formula:

$$A \approx \frac{3}{4}k_B T\left(\frac{\varepsilon_1-\varepsilon_3}{\varepsilon_1+\varepsilon_3}\right)\left(\frac{\varepsilon_2-\varepsilon_3}{\varepsilon_2+\varepsilon_3}\right) + \frac{3h}{4\pi}\int_{v_1}^{\infty}\left(\frac{\varepsilon_1(iv)-\varepsilon_3(iv)}{\varepsilon_1(iv)+\varepsilon_3(iv)}\right)\left(\frac{\varepsilon_2(iv)-\varepsilon_3(iv)}{\varepsilon_2(iv)+\varepsilon_3(iv)}\right)dv,$$

where $\in_1$, $\in_2$ and $\in_3$ are static (DC) dielectric constants of the particle, endothelial cells and the liquid component of the blood (plasma), respectively; $\in_1(iv)$, $\in_2(iv)$ and $\in_3(iv)$ are values dielectric functions at imaginary frequencies for the particle, endothelial cells and the liquid component of the blood (plasma), respectively; $v_1=2\pi k_B T/h$, h is Planck's constant. The dielectric functions and constants can be evaluated using dielectric spectroscopy as disclosed in C. Prodan, F. Mayo, J. R. Claycomb, and J. H. Miller, Jr., M. J. Benedik, *Low-frequency, low-field dielectric spectroscopy of living cell suspensions*, Journal of Applied Physics (Apr. 1, 2004) Volume 95, Issue 7, pp. 3754-3756. A typical value for the Hamaker constant in liquids is around $10^{-20}$ Joules, see, e.g., Israelachvili, J. 1992. Intermolecular and Surface Forces, 2nd ed. Academic Press, New York.

$\rho_\infty$ is the ionic concentration of blood. A typical value for the ionic concentration for blood can be around 150 mM, see, for example, Ganong, W. F. Review of Medical Physiology, 21st ed. New York: Lange Medical Books/McGraw-Hill Medical Publishing Division, 2003.

$\kappa^{-1}$ is the Debye length, i.e., a length over which mobile charge carriers (e.g., electrons) can screen out electric fields. Generally, in an electrolyte such as blood, the Debye length can be determined using the following formula $$\kappa^{-1} = \sqrt{\frac{\varepsilon_o \varepsilon_r k_B T}{2N_A e^2 I}}$$

where $\in_0$ is the permittivity of free space, $\in_r$ is a dielectric constant of the electrolyte, $k_B$ is Boltzmann's constant, T is the absolute temperature, e is the charge on an electron, I is the ionic strength of the electrolyte, $N_A$ is Avogadro's number. For blood, the Debye length can be around 0.8 nm.

$\Gamma$ is the number of polymer chains per unit area. $\Gamma=s^{-2}$, where s is the mean separation distance s between two adjacent chains on the surface of the nanoparticle. The separation distance s depends on the size of the functional groups at the nanoparticle surface and on the size of the polymer chains (molecular weight) conjugated to this functional groups. The separation distance s can be estimated by citofluorimetric exams, see for example Jacob N. Israelachvili, Intermolecular and Surface Forces, Second Edition: With Applications to Colloidal and Biological Systems, Academic Press; II Edition, 1992.

$R_g$ is a radius of gyration of a polymer such as a ligand. $R_g$ can be related to the number N of repeat units of the polymer forming a chain of the polymer and the effective length of the repeat unit, l. $R_g$ also depends on the polymer's solvent. For an ideal solution, i.e. a solution, where the interaction (attractive repulsive) between the repeat units of the polymers is negligible, $$R_g = l\sqrt{\frac{N}{6}}.$$

For a "good" solvent, i.e. a solvent with repulsion between the segments, $R_g=lN^{3/5}$; for a "bad" solvent, i.e. a solvent with attractive interaction between the repeat units, $R_g=lN^{1/3}$, see e.g. Jacob N. Israelachvili, *Intermolecular and Surface Force: With Applications to Colloidal and Biological Systems*, Academic Press; Second Edition, 1992. The liquid component of blood (plasma) is an aqueous solution and water is a good solvent for PEG polymers.

$z_v$ and $z_c$ are electrostatic surface potentials at the surface of the particle and at the surface of the target site respectively. $\in_v$ and $\in_c$ can be estimated using Zetasizer™ Nano series instrument from Malvern Instruments, Worcestershire United Kingdom.

The endocytosis maximizing radius can be determined as a value of R, for which a wrapping time $t_w$ is minimized. For the cylindrical particle, the wrapping time can be written as $$t_w = \frac{1}{M}\left(\frac{\pi R}{2\alpha}\right)^2, \quad (5)$$

where M is a lateral mobility of membrane receptors.

$t_w$ has a minimum because $t_w$, on one hand, grows with growing R and, on the other hand, reduces with increasing $\alpha$, which in turn grows with increasing R. The endocytosis maximizing radius can be determined by introducing into equation (5) α as a function of R from equation (1) and determining a value of R, for which $t_w$ is minimized. The determination of the endocytosis maximizing radius can be performed using numerical or graphical methods within the skills of those practicing the art.

Table 1 presents common ranges for dimensionless parameters $\tilde{\xi}$; $\hat{m}$; G; F; H and L.

TABLE 1

| | |
|---|---|
| $\tilde{\xi}$ | 2 |
| $\hat{m}$ | $10^{-4}$--$10^{-1}$ |
| G | 1--$10^2$ |
| F | −500--500 |
| H | $10^{-3}$--$10^{-1}$ |
| L | $10^{-4}$--$10^{-1}$ |

Based on the small values for L compared to values of $\tilde{s}_{eq}$, L can be disregarded, i.e., taken equal to 0, in equations (1) and (2).

Figure 2:
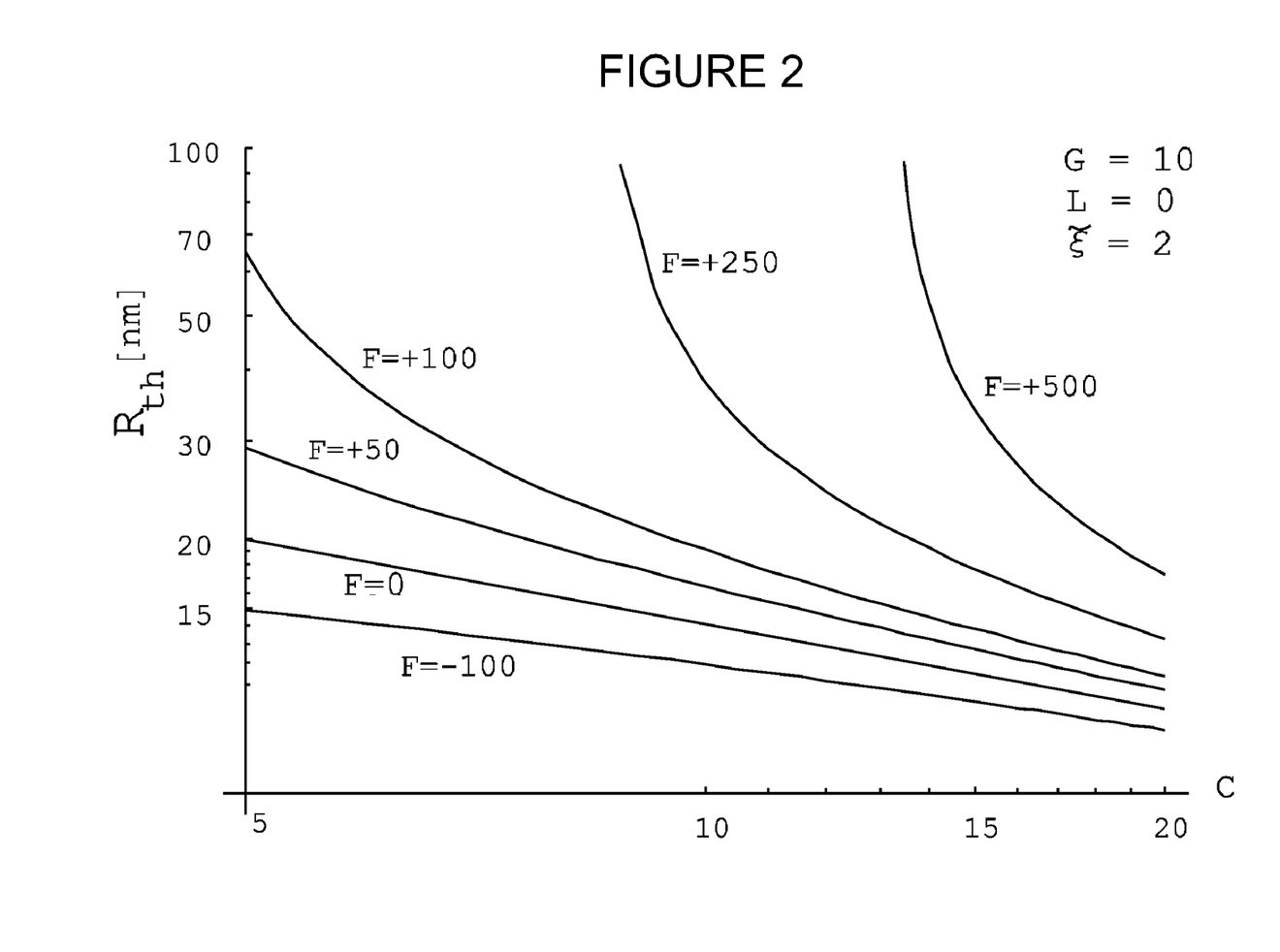
FIG. 2 shows a variation of an endocytosis threshold radius $R_{th}$ for a cylindrical particle as a function of a binding energy for different values of a non-specific parameter F.

FIG. 2 presents graphs of a variation of the endocytotic threshold radius $R_{th}$ with the bonding energy factor C for different values of the non-specific parameter F varying from −100 to +500, G=10, L=0. The results are compared with those predicted by Gao et al. Proc. Natl. Acad. Sci. USA, 2005 5; 102(27):9469-74, 2005, with $\tilde{\xi}$=2, B=20 and $m_b$=5×10$^3$ μm$^{-2}$ (F=0 curve). As C increases, the threshold radius reduces steadily. If the non-specific parameter F changes within the common range of variation (see Table 1), the threshold radius is significantly affected. Repulsive non-specific interactions (F>0) increase the threshold radius. For C=15, G=10 and F=0 Gao et al. predicts a threshold radius of about 12 nm, while according to the present invention for F=500 the threshold radius is about 35 nm with the rest of the parameters being the same. The variation of the threshold parameter compared with the results predicted by Gao is even larger as G increases.

Figure 3:
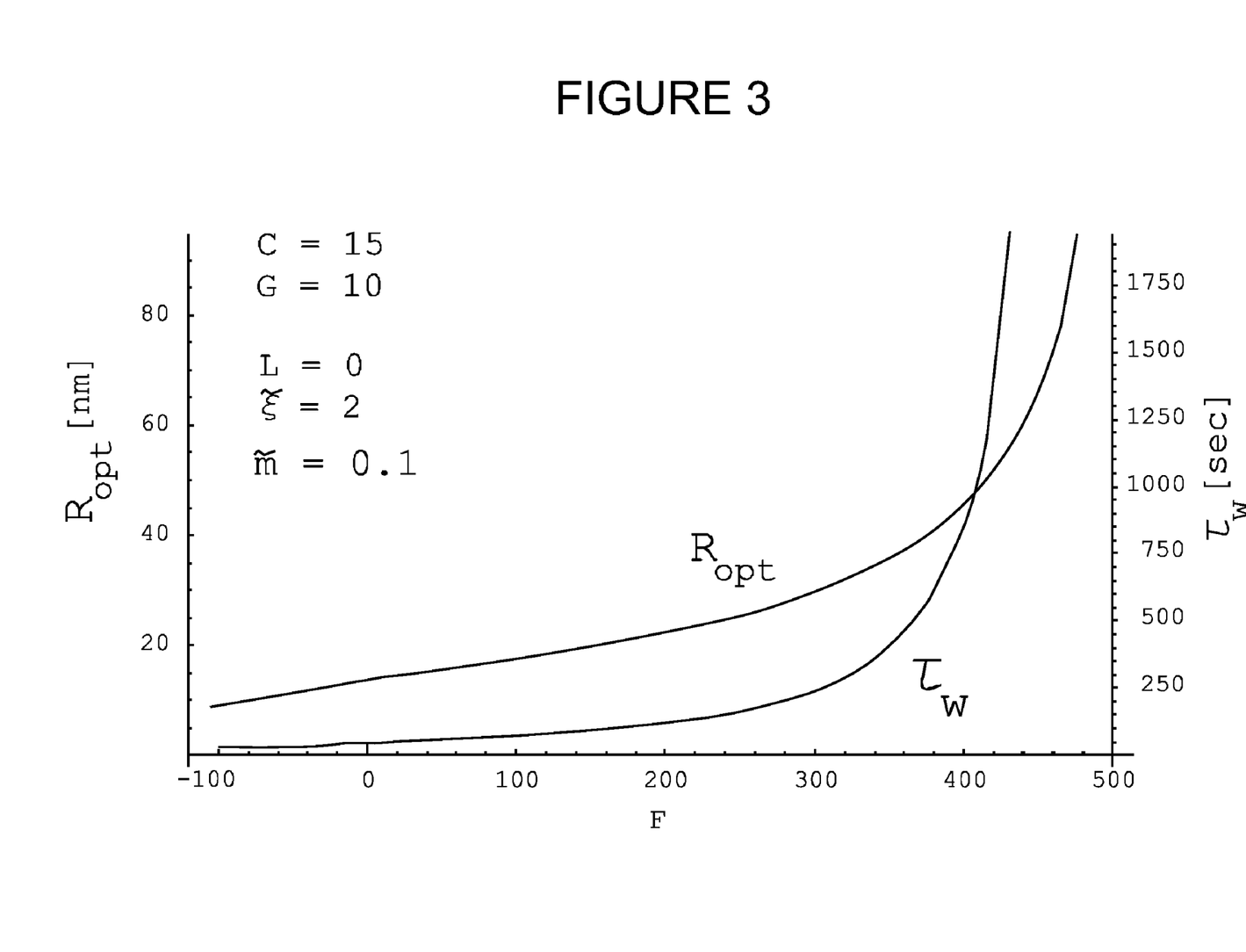
FIG. 3 shows an endocytosis maximizing radius $R_{opt}$ for a cylindrical particle and a corresponding wrapping time $t_w$ as a function of a non-specific parameter F.

FIG. 3 demonstrates the effect of the non-specific parameter F on the endocytosis maximizing radius $R_{opt}$ and the wrapping time $t_w$ for C=15, G=10 and $\hat{m}$=0.1. As the repulsive interactions between the particle and the cell become stronger, i.e., F increases, the endocytosis maximizing radius and the wrapping time increase. For F=0, which corresponds to the results of Gao et al., the endocytosis maximizing radius is about 14 nm and a wrapping time is about 35 sec, while for F=100, the endocytosis maximizing radius becomes about 18 nm and the wrapping time about 60 sec and for F=500, the endocytosis maximizing radius becomes 130 nm and the wrapping time becomes 18 h.

Particles

An endocytotic particle is a particle having a radius greater than the endocytosis threshold size or radius that is determined as discussed above. Preferably, the endocytotic particle has a size or radius substantially equal to the endocytois maximizing radius that is determined as discussed above. "Substantially equal" means that the radius of the selected particle equals the endocytosis maximizing radius within a certain margin. In some embodiments, such a margin can be, for example, 30% or less, i.e., the radius or the size of the endocytotic particle is from 0.7 to 1.3 of the endocytosis maximizing radius. In some embodiments, the margin can be 20% or less or 10% or less or 5% or less or 3% or less or 1% or less.

An endocytotic particle can be a micro or nanoparticle of any type. For example, the particle can be a liposome, a polymer-based particle, a silicon-and silica based particle, a quantum dot, a gold nanoshell or a dendrimer.

Endocytotic particles can be fabricated to have a specific radius or alternatively endocytotic particles can be screened from a pool of particles having a broad distribution of sizes. The selection from the pool of particles can be performed, for example, using Zetasizer™ Nano series instrument from Malvern Instruments, Worcestershire, United Kingdom, which allows measuring radii of the particles.

The endocytotic particle can be fabricated by any method. Preferably, the fabrication method provides a control over the size of the particle.

For example, in some embodiments, the particles can be fabricated by a top-down microfabrication or nanofabrication methods, such as photolithography, electron beam lithography, X-ray lithography, deep UV lithography or nanoprint lithography. The advantage of using the top-down fabrication methods can be that such methods provide for a scaled up production of particles that are uniform in dimensions.

The endocytotic particles can have on their surfaces targeting moieties, such as ligands, aptamers or antibodies. For example, ligands can be chemically linked to appropriate reactive groups on the surface of the particles. Protein ligands can be linked to amino- and thiol-reactive groups under conditions effective to form thioether or amide bonds respectively. Methods for attaching antibody or other polymer binding agents to an inorganic or polymeric support are detailed, for example, in Taylor, R., Ed., Protein Immobilization Fundamentals and Applications, pp. 109110 (1991).

In some embodiments, the endocytotic particle can have one or more channels connecting a reservoir with the surface. In some embodiments, the reservoir and the channels can be pores in the body of the particle. In such case, the particle can comprise a porous or nanoporous material. The pores of the porous or nanoporous material can be controlled to achieve a desired load of the active agent and a desired release rate. The nanoporous material with controllable pore size can be an oxide material, such as $SiO_2$, $Al_2O_3$, or $TiO_2$. Fabrication of nanoporous oxide particles, also known as sol gel particles, is detailed, for example, in Paik J. A. et. al. J. Mater. Res., Vol. 17, August 2002. The nanoporous material with controllable pore size can be also nanoporous silicon. For details of fabrication of nanoporous silicon particles, see Cohen M. H. et. al. Biomedical Microdevices 5:3, 253-259, 2003.

In other embodiments, the endocytotic particle has no channels at all. Such particle can comprise, for example, a biodegradable material. For example, the particle may be formed of metals, such as iron, titanium, gold, silver, platinum, copper, and alloys and oxides thereof. The biodegradable material can be also a biodegradable polymer such as polyorthoesters, polyanhydrides, polyamides, polyalkylcyanoacrylates, polyphosphazenes, and polyesters. Exemplary biodegradable polymers are described, for example, in U.S. Pat. Nos. 4,933,185, 4,888,176, and 5,010,167. Specific examples of such biodegradable polymer materials include poly(lactic acid), polyglycolic acid, polycaprolactone, polyhydroxybutyrate, poly(N-palmitoyl-trans-4-hydroxy-L-proline ester) and poly(DTH carbonate).

In still other embodiments, the particle is an active agent per se.

Active Agent

The active agent can be a therapeutic compound or an imaging agent. The selection of the active agent depends on the desired application.

The therapeutic agent may be any physiologically or pharmacologically active substance that can produce a desired biological effect in fenestrated vasculature of the subject, such as a mammal or a human. The therapeutic agent may be any inorganic or organic compound, without limitation, including peptides, proteins, nucleic acids, and small molecules. The therapeutic agent may be in various forms, such as an unchanged molecule, molecular complex, pharmacologically acceptable salt, such as hydrochloride, hydrobromide, sulfate, laurate, palmitate, phosphate, nitrite, nitrate, borate, acetate, maleate, tartrate, oleate, salicylate, and the like. For acidic therapeutic agent, salts of metals, amines or organic cations, for example, quaternary ammonium, can be used. Derivatives of drugs, such as bases, esters and amides also can be used as a therapeutic agent. A therapeutic agent that is water insoluble can be used in a form that is a water soluble derivative thereof, or as a base derivative thereof, which in either instance, or by its delivery, is converted by enzymes, hydrolyzed by the body pH, or by other metabolic processes to the original therapeutically active form.

The therapeutic agent can be a chemotherapeutic agent, an immunosuppressive agent, a cytokine, a cytotoxic agent, a nucleolytic compound, a radioactive isotope, a receptor, and a pro-drug activating enzyme, which may be naturally occurring or produced by synthetic or recombinant methods, or any combination thereof.

Drugs that are affected by classical multidrug resistance, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) can have particular utility as the therapeutic agent.

A cancer chemotherapy agent can be also a preferred therapeutic agent. Useful cancer chemotherapy drugs include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Useful cancer chemotherapy drugs also include alkylating agents such as Thiotepa and cyclosphosphamide; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitrogen mustards such as Chlorambucil, Chlomaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Carminomycin, Carzinophilin, Chromomycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues, such as Denopterin, Methotrexate, Pteropterin, and Trimetrexate; purine analogs, such as Fludarabine, 6-mercaptopurine, Thiamiprine, and Thioguanine; pyrimidine analogs, such as Ancitabine, Azacitidine, 6-azauridine, Carmofur, Cytarabine, Dideoxyuridine, Doxifluridine, Enocitabine, Floxuridine, and 5-FU; androgens, such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs, such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylomithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

Cytokines can be also used as the therapeutic agent. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The imaging agent can be any substance that can provide imaging information about a targeted site in a body of an animal such a mammal or a human being. The imaging agent can comprise magnetic material, such as iron oxide, for magnetic resonance imaging. For optical imaging, the active agent can be, for example, semiconductor nanocrystal or quantum dot. For optical coherence tomography imaging, the imaging agent can be metal, e.g. gold or silver, nanocage particles. The imaging agent can be also an ultrasound contrast agent such as a micro or nanobubble or iron oxide micro or nanoparticle.

Compositions

The endocytotic particles can be part of a composition, such as a pharmaceutical composition. Such a composition can be a suspension comprising the endocytotic particles described above for use in administering a therapeutic or imaging agent. To form the suspension, the particles can be suspended in an aqueous medium at a selected concentration. The optimal concentration will depend on the characteristics (e.g., solubilization properties) of the particle, type of therapeutic application and mode of administration. For example, compositions for oral administration can be relatively viscous, and may therefore contain a high concentration (e.g., >50%) of the particle. Solutions for bolus injections preferably contain a relatively concentrated suspension of the particles (e.g., 10-50%), but not so concentrated that it has an appreciably higher viscosity than saline (to minimize need for large-bore needles). The solution used for continuous intravenous infusion typically contains a relatively low concentration (e.g., 2-10% suspension) of the particles, due to the relatively large volumes of fluid that are administered.

The particles can be suspended in any suitable aqueous carrier vehicle. A suitable pharmaceutical carrier is one that is non-toxic to the recipient at the dosages and concentrations employed and is compatible with other ingredients in the formulation. Examples of suitable carrier vehicles include but are not limited to water, saline, Ringer's solution, dextrose solution, and 5% human serum albumin. Suspensions for use in injectable formulations are preferably isotonic with the subject's blood. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients.

Prior to administration to a subject, the suspension of particles can be sterilized by a suitable sterilization method. Particles fabricated from a heat-stable material can be heat-sterilized, e.g., using an autoclave. Particles fabricated from a not heat-stable material may be sterilized by passage through a commercially-available sterilization filter, e.g., a 0.2 µm filter. Of course, filtration may be used only in cases where the particles is smaller than the pores of the sterilizing filter.

The particles can be administered to a subject in need of therapeutic intervention via any suitable administration method. The particular method employed for a specific application is determined by the attending physician. The particles can be administered by one of the following routes: topical, parenteral, inhalation, oral, vaginal and anal. Intravascular administration, which includes intravenous (i.v.), intramuscular (i.m.) and subcutaneous (s.c.) injection, may be particularly preferred. Intravascular administration can be either local or systemic. Local intravascular delivery can be used to bring the particles in the vicinity of a body site having a known tumor or inflammation by use of guided catheter system, such as a CAT-scan guided catheter. General injection, such as a bolus i.v. injection or continuous/trickle-feed i.v. infusion are typically systemic.

The endocytotic particles are injected into the blood stream and allowed to circulate and localize to their target site. Preferably, the endocytotic particles are injected to a vasculature of the target site.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of enhancing an endocytosis of an active agent into a cell having surface receptors, comprising:
    obtaining particles comprising the active agent and surface moieties that have an affinity for or are capable of binding to the receptors,
    wherein the particles have a radius no less than an endocytotic threshold radius that is based on (a) a surface density of the receptors, (b) a surface density of the moieties and (c) one or more interaction parameters, including at least one of a non-specific interaction strength between the cell and one of said particles selected from the group consisting of decay length ($\delta$), ligand-receptor natural length ($\xi$), ligand-receptor spring constant (k), ligand-receptor binding energy (C) and stiffness ($\sigma$), and wherein the particles have a radius that is from 0.7 to 1.3 of the particles' endocytosis maximizing radius; and
    interacting the cell with the particles, wherein the interacting enhances the endocytosis.

2. The method of claim 1, wherein the cell is an endothelial cell.

3. The method of claim 2, wherein the endothelial cell is an endothelial vasculature cell.

4. The method of claim 3, wherein the receptors are angiogenesis vasculature receptors, coopted vasculature receptors or renormalized receptors.

5. The method of claim 1, wherein the surface moieties are selected from the group consisting of ligands, aptamers, antibodies and combinations thereof.

6. The method of claim 1, wherein the one or more interaction parameters further comprise the spring constant between said receptors and said moieties.

7. The method of claim 1, wherein the obtaining comprises selecting the particles from a unselected particle population.

8. The method of claim 1, wherein the obtaining comprises fabricating the particles.

9. The method of claim 8, wherein the fabricating comprises fabricating by a top-down process.

10. The method of claim 8, wherein the fabricating comprises disposing the moieties onto a surface of the particles.

11. The method of claim 1, wherein the active agent comprises an imaging agent or a therapeutic agent.

12. The method of claim 1, wherein the particles are cylindrical particles.

13. The method of claim 1, wherein the particles are spherical particles.

14. The method of claim 1, wherein the particles comprise a nanoporous material.

15. The method of claim 14, wherein the nanoporous material is a nanoporous silicon or a nanoporous oxide material.

16. A composition comprising particles, wherein the particles comprise:
   an active agent; and
   surface moieties, wherein the surface moieties have an affinity for or are capable of binding to receptors on a cell, and wherein the particles have a radius no less than an endocytotic threshold radius that is based on (a) a surface density of the receptors, (b) a surface density of the moieties and (c) one or more interaction parameters, including at least one of a non-specific interaction strength between the cell and one of said particles selected from the group consisting of decay length ($\delta$), ligand-receptor natural length ($\xi$), ligand-receptor spring constant (k), ligand-receptor binding energy (C) and stiffness ($\sigma$), and wherein the particles have a radius that is from 0.7 to 1.3 of the particles' endocytosis maximizing radius.

17. A method of treating or monitoring a physiological condition comprising:
   selecting a target site affected by the condition in a body of a subject in need thereof such that the target site has surface receptors; and
   administering to a subject in need thereof an effective amount of particles, wherein the particles comprise an active agent and surface moieties, wherein the surface moieties have an affinity for or are capable of binding to receptors on a cell, and wherein the particles have a radius no less than an endocytotic threshold radius that is based on (a) a surface density of the receptors, (b) a surface density of the moieties, and (c) one or more interaction parameters, including at least one of a non-specific interaction strength between the cell and one of said particles selected from the group consisting of decay length ($\delta$), ligand-receptor natural length ($\xi$), ligand-receptor spring constant (k), ligand-receptor binding energy (C) and stiffness ($\sigma$), and wherein the particles have a radius that is from 0.7 to 1.3 of the particles' endocytosis maximizing radius.

18. A method of treating or monitoring a physiological condition comprising:
   selecting a target site affected by the condition in a body of a subject in need thereof such that the target site has surface receptors; and
   administering to the subject an effective amount of a composition comprising particles that comprise at least one active agent and that have a surface with moieties that have affinity for or are capable of binding to the receptors, wherein at least 10% of the particles have a radius substantially equal to an endocytosis maximizing radius that is based on a surface density of the receptors, a surface density of the moieties and one or more interaction parameters including at least one of a non-specific interaction strength between cells of said target site and one of said particles selected from the group consisting of decay length ($\delta$), ligand-receptor natural length ($\xi$), ligand-receptor spring constant (k), ligand-receptor binding energy (C) and stiffness ($\sigma$), and wherein the particles have a radius that is from 0.7 to 1.3 of the particles' endocytosis maximizing radius.

19. The method of claim 18, wherein at least 50% of the particles have a radius substantially equal to the endocytosis maximizing radius.

20. The method of claim 18, wherein the target site is a vasculature site.

21. The method of claim 20, wherein the vasculature site is a coopted vasculature site, a angiogenesis vasculature site or a coopted vasculature site.

22. The method of claim 18, wherein the at least one active agent comprises an imaging agent, a therapeutic agent or a combination thereof.

23. The method of claim 18, wherein the selected particles are cylindrical particles.

24. The method of claim 18, wherein the selected particles are spherical particles.

25. The method of claim 18, wherein the selected particles comprise a nanoporous material.

26. The method of claim 25, wherein the nanoporous material is a nanoporous silicon or a nanoporous oxide material.

27. The method of claim 18, wherein the subject is a human.

28. The composition of claim 16, wherein the active agent comprises an imaging agent or a therapeutic agent.

29. The composition of claim 16, wherein the surface moieties are selected from the group consisting of ligands, aptamers, antibodies and combinations thereof.

30. The composition of claim 16, wherein the one or more interaction parameters further comprise the spring constant between said receptors and said moieties.

31. The method of claim 17, wherein the one or more interaction parameters further comprise the spring constant between said receptors and said moieties.

32. The method of claim 18, wherein the subject is a human.

* * * * *